United States Patent
Park et al.

(10) Patent No.: US 12,024,751 B2
(45) Date of Patent: Jul. 2, 2024

(54) METHOD FOR PRODUCING PSICOSE

(71) Applicant: SAMYANG CORPORATION, Seoul (KR)

(72) Inventors: Ji Won Park, Suwon-si (KR); Sung Won Park, Yongin-si (KR); Hye Jung Kim, Incheon (KR); Chong Jin Park, Daejeon (KR); Kang Pyo Lee, Seoul (KR)

(73) Assignee: SAMYANG CORPORATION, Seoul (KR)

( * ) Notice: Subject to any disclaimer, the term of this patent is extended or adjusted under 35 U.S.C. 154(b) by 1086 days.

(21) Appl. No.: 16/464,356

(22) PCT Filed: Nov. 24, 2017

(86) PCT No.: PCT/KR2017/013541
§ 371 (c)(1),
(2) Date: Jan. 12, 2021

(87) PCT Pub. No.: WO2018/105933
PCT Pub. Date: Jun. 14, 2018

(65) Prior Publication Data
US 2023/0046104 A1  Feb. 16, 2023

(30) Foreign Application Priority Data
Dec. 8, 2016 (KR) .................. 10-2016-0167049

(51) Int. Cl.
*C13K 13/00* (2006.01)
*B01D 15/18* (2006.01)
(Continued)

(52) U.S. Cl.
CPC .......... *C13K 13/007* (2013.01); *B01D 15/185* (2013.01); *B01D 15/1871* (2013.01);
(Continued)

(58) Field of Classification Search
CPC .... C13K 13/007; C13K 11/00; B01D 15/185; B01D 15/1871; B01D 15/242;
(Continued)

(56) References Cited

U.S. PATENT DOCUMENTS 2,985,589 A    5/1961  Broughton et al.
11,202,460 B2 * 12/2021  Park .................. A23L 29/30
(Continued)

FOREIGN PATENT DOCUMENTS

CN    103146849 A  *  6/2013  ............. C08B 30/02
EP    3378943         9/2018
(Continued)

OTHER PUBLICATIONS

Translation of Kang (KR20160062349A A) (Year: 2016).*
(Continued)

*Primary Examiner* — Ekandra S. Miller-Cruz
(74) *Attorney, Agent, or Firm* — LEX IP MEISTER, PLLC (57) ABSTRACT

The present invention relates to a method for effectively utilizing fructose raffinate obtained in the process for separating psicose conversion product with a high purity chromatography in the process for preparing psicose, and more specifically, it is utilized for preparation of fructose-containing raw material solution for preparing psicose by supplying the fructose raffinate obtained in the separation step of psicose preparation into the psicose conversion reaction.

16 Claims, 3 Drawing Sheets

(51) Int. Cl.
*B01D 15/24* (2006.01)
*B01D 15/36* (2006.01)
*C13K 11/00* (2006.01)

(52) U.S. Cl.
CPC ......... *B01D 15/242* (2013.01); *B01D 15/362* (2013.01); *C13K 11/00* (2013.01)

(58) Field of Classification Search
CPC .............. B01D 15/362; B01D 15/1828; B01D 15/361; C07H 1/06; C07H 3/02; C12P 19/02
USPC ......................................................... 127/42
See application file for complete search history.

(56) References Cited

U.S. PATENT DOCUMENTS

| | | | |
|---|---|---|---|
| 11,248,015 B2* | 2/2022 | Park | ......................... C07H 1/06 |
| 11,358,980 B2* | 6/2022 | Park | ..................... B01D 15/361 |
| 2017/0313734 A1* | 11/2017 | Kim | ..................... B01D 9/0036 |

FOREIGN PATENT DOCUMENTS

| | | |
|---|---|---|
| JP | H06-277099 | 10/1994 |
| JP | 2011-206054 | 10/2011 |
| JP | 2019-536822 | 12/2019 |
| JP | 2020-500557 | 1/2020 |
| KR | 10-2006-0125971 | 12/2006 |
| KR | 10-0967093 | 7/2010 |
| KR | 10-1318422 | 10/2013 |
| KR | 10-2014-0021974 | 2/2014 |
| KR | 10-2014-0054997 | 5/2014 |
| KR | 10-2014-0080282 | 6/2014 |
| KR | 10-2015-0021065 | 2/2015 |
| KR | 10-2016-0046143 | 4/2016 |
| KR | 10-2016-0062349 | 6/2016 |
| KR | 10-2017-0057078 | 5/2017 |
| TW | 201619177 | 6/2016 |
| WO | 2014-049373 | 4/2014 |
| WO | 2014-168302 | 10/2014 |
| WO | 2015-182937 | 12/2015 |
| WO | 2016-061037 | 4/2016 |
| WO | 2016-064087 | 4/2016 |
| WO | 2018-127668 | 7/2018 |

OTHER PUBLICATIONS

N. Wagner et al., "Model-based cost optimization of a reaction-separation integrated process for the enzymatic production of the rare sugar D-psicose at elevated temperatures", Chemical Engineering Science, 2015, vol. 137, p. 423-435.
EPO, Supplementary European Search Report of EP 17877459.2 dated Jun. 30, 2020.
Nina Wagner, "Integration of biocatalysis and simulated moving bed chromatography for the high-yield production of rare sugars", Doctoral Thesis, ETH Zurich, XP055512035.
Nguyen et al, "Separation of D-psicose and D-fructose Using Simulated Moving Bed Chromatography", Master's Thesis, Inha University, KR, Jan. 31, 2009, pp. 1-61, XP009515174.
Matthias Bechtold et al., "Integrated operation of continuous chromatography and biotransformations for the generic high yield production of fine chemicals", Journal of Biotechnology, Elsevier, Amsterdam, NL, vol. 124, No. 1, pp. 146-162, (Jun. 25, 2006), XP024956758.
Applied technology of bioreactor (Jan. 10, 1986), p. 120-127 with the English translation of the cited part.
Physical and chemistry dictionary published by Iwanami (May 20, 1971), p. 1345, 1090, 896, 597 with the English translation of the cited part.
Dictionary of starch science (Oct. 25, 2010), p. 464-469 with the English translation of the cited part.
Wagner, Nina, "Integration of biocatalysis and simulated moving bed chromatography for the high-yield production of rare sugars", Doctoral thesis of Swiss Federal Institute of Technology Zurich, Doctor of Science of ETH Zurich, 2014.
Nguyen, Van Duc Long, "Separation of D-psicose and D-fructose Using Simulated Moving Bed Chromatography", Master's thesis of Inha University, pp. 1-61, Feb. 2009.
Wagner, N. et al., Multi-objective optimization for the economic production of d-psicose using simulated moving bed chromatography, Journal of Chromatography A, 2015, vol. 1398, pp. 47-56.
Nguyen, Van Duc Long et al., "Separation of D-psicose and D-fructose using simulated moving bed chromatography", Journal of Separation Science, 2009, vol. 32, pp. 1987-1995.

* cited by examiner

METHOD FOR PRODUCING PSICOSE

TECHNICAL FIELD

The present invention relates to a utilization of fructose raffinate obtained in psicose preparation process, and more specifically, a method and an apparatus of preparing psicose by using the fructose raffinate obtained in the psicose preparation process as fructose-containing raw material.

BACKGROUND ART

Psicose is an epimer of fructose (D-fructose) and is one kind of functional saccharides known as a rare saccharide, and it has been known to have an effect on prevention and improvement of diabetes, since it has sweetness of about 60 to 70% of sugar and almost zero calorie. In addition, psicose is known to have excellent solubility, and it is one of materials where utilization for food is attracting attention.

There are a chemical method and a biological method in the method for preparing psicose, and recently, a method for preparing psicose with a biological method performs psicose conversion reaction by contacting fructose-containing substrate solution with a psicose epimerase or a microorganism producing the enzyme.

However, it is required to separate psicose with high purity, since the reaction solution comprising D-psicose is low purity product. In fact, various methods have been applied to separate industrially produced materials with high purity, and in case of sugar, a product is produced by crystallization after making high purity solution mainly by using a chromatography, to obtain psicose crystals.

To obtain psicose with high purity from the psicose conversion product, it is required to separate psicose with high purity. Since not only psicose but also fructose raffinate including fructose at a high concentration are produced in the psicose separation process, a method for enhancing the purity and yield of psicose and increasing the availability of raw material by recycling the fructose raffinate is required.

DISCLOSURE

Technical Problem

One example of the present invention is to provide a method and an apparatus for preparing psicose by recycling fructose raffinate obtained in the psicose separation process for a reactant for psicose conversion reaction, in order to the purity and the yield of psicose by recycling fructose raffinate.

Another embodiment of the present invention is to provide a method and an apparatus for preparing psicose by controlling ion concentration of fructose raffinate obtained in the psicose separation process for a reactant for psicose conversion reaction.

Technical Solution

An embodiment of the present invention relates to a method and an apparatus for preparing psicose comprising recycling fructose raffinate obtained in the psicose separation process for a reactant for psicose conversion reaction. The fructose raffinate containing fructose at a high concentration is produced in the psicose separation process, and thus is reused for enhancing the purity and yield of psicose and increasing the availability of raw material.

An embodiment of the present invention relates to a method of preparing psicose, comprising steps of separating psicose-conversion product with a simulated moving bed (SMB) chromatography to obtain psicose fraction and fructose raffinate, and recycling the fructose raffinate as a raw material of psicose conversion reaction. In the present invention, the fructose raffinate obtained in the SMB chromatograph or processing product thereof can be used as the fructose-containing raw material to be put into the psicose conversion reaction. The fructose-containing raw material in the present invention means the fructose raffinate obtained in the SMB chromatograph of psicose conversion product or processed product thereof alone (hereinafter, first fructose reactant), and a mixture thereof with new fructose-containing raw material which is not used before (hereinafter, second fructose reactant). The processed product of fructose raffinate may be various fructose-containing raw material or reactant which may be obtained by treating with various processes, and for examples, may be product obtained by treating with one or more steps selected from the group consisting of cooling, pH treatment, ion purification and concentration.

In an embodiment, the fructose raffinate obtained in the high-purity separation process may be used for reactant of psicose conversion reaction, for example, by treating ion purification and concentration simultaneously or sequentially.

When the fructose raffinate obtained in the psicose separation process is directly provided into the psicose conversion process, excessive cations, especially calcium ion, are contained due to the influence of the strong acid resin used in the simulated moving bed chromatographic separation step. It may have a bad influence on the psicose conversion reaction. Therefore, the fructose raffinate can be ion-purified to adjust the calcium ion concentration to a specific concentration range or below, or to control the cation concentration to below the specific value of electric conductivity.

In an embodiment of the present invention, the method may include a step of ion purification before the fructose raffinate is added to the psicose conversion reaction, so that the calcium ion concentration of the fructose raffinate or the mixture of the fructose raffinate with fresh fructose starting material can be preferably adjusted to 0.05 mM or lower. Further, the method may include a step of ion purification before the fructose raffinate is added to the psicose conversion reaction, so that the electric conductivity of the processed fructose raffinate or the mixture of the fructose raffinate with fresh fructose starting material can be preferably adjusted to 0 to 15 μs/cm.

An embodiment of the present invention is to provide an apparatus of preparation for a psicose comprising a psicose conversion reactor for performing psicose conversion reaction from fructose-containing raw material: a simulated moving bed (SMB) chromatography separator which comprises a column packed with cation exchange resin having an active group, a feed inlet and an outlet for discharging a psicose fraction and a fructose raffinate: a fructose separation device for separating fructose from the fructose raffinate discharged from the chromatography separator; an ion-purifier equipped with a column packed with ion exchange resin; and a concentrator, wherein the processed product obtained from the concentrator is recycled into the psicose conversion reactor.

The present invention efficiently prepares psicose by using fructose raffinate, preventing the product being deteriorated by mixing the fructose isomerization product with fructose raffinate, and maintains the fructose content of fructose syrup used for psicose production.

Hereinafter, the present invention will be described in more detail.

The method for preparing psicose includes a step of obtaining the psicose fraction and fructose raffinate in step of separating the psicose conversion product with the SMB chromatography and recycling the fructose raffinate as a reactant for the psicose conversion reaction.

In one specific embodiment, the method for preparing psicose comprises (1) a psicose conversion step of preparing psicose-conversion product by performing biological conversion reaction of a fructose-containing raw material; (2) a psicose separation step of obtaining psicose fraction and fructose raffinate by performing ion purification and separation with a SMB chromatography of the psicose conversion product; and (3) a step of using the fructose raffinate as fructose-containing reactant by putting the fructose raffinate, and optionally a step of obtaining psicose crystal using the psicose fraction.

The process of preparation of psicose of the present invention may use both continuous and batch processes, preferably a continuous process.

In the present specification, the term "raffinate" is also called as "residual solution". The products obtained from as a separation process which is provided by a feeding material include two fraction of a target fraction including a target material to increase its content by the separation process and a residual solution including a material to be removed or to reduce its content. In one embodiment of the present invention, the product obtained in the psicose conversion process is a mixture of fructose as a raw material and psicose as a product material. After the psicose conversion product is passed through the SMB chromatograph separation, the psicose fraction with increased content of psicose and the residual solution are produced. The fructose raffinate can be obtained, since fructose used as a reacting raw material is included at a large amount in the residual solution.

Hereinafter, the process of psicose preparation including the recycling of fructose raffinate obtained in the high purity separation process for the psicose conversion product according to the present invention will be described in detail by each step.

(1) Psicose Conversion Process

The psicose conversion process is a process for obtaining psicose from the fructose-containing raw material by performing a psicose conversion reaction, and produces a reaction solution including psicose as reaction product converted from fructose.

In one specific embodiment of the present invention, the method for preparing psicose according to a biological method may culture a strain producing psicose epimerase or a recombinant strain including a gene encoding the psicose epimerase and react the psicose epimerase obtained from that with a fructose-containing raw material to produce psicose. The psicose epimerase reaction may be performed in a liquid phase reaction or a solid phase using an immobilization enzyme.

Otherwise, psicose may be produced by obtaining a strain producing psicose epimerase or a recombinant strain including a gene encoding the psicose epimerase, and reacting the fructose-containing raw material with a composition for psicose preparation comprising one or more selected from the group consisting of microbial cell of the strain, culture of the strain, lysate of the strain, and extract of the lysate or culture. When psicose is prepared by using the microbial cell of strain producing the psicose epimerase, it may be performed with a liquid phase reaction or a solid phase using an immobilized microbial cell.

In one specific embodiment of the present invention, the strain producing the psicose epimerase may be the strain which has high stability and can convert fructose to psicose at a high yield or produce the psicose epimerase. The strain may be a strain isolated from nature or its mutant strain, non-GMO strain, or a recombinant strain in which a gene encoding the psicose epimerase is introduced. In one embodiment of the present invention, various known strains as the non-GMO strain may be used. The recombinant strain may be prepared by using various host cells, for example, *E. coli, Bacillus* sp. strain, *Salmonella* sp. strain and *Corynebacterium* sp. strain, etc, but preferably, GRAS strain such as *Corynebacterium* sp. Strain, and may be *Corynebacterium glutamicum*.

The psicose conversion process according to the one embodiment of the present invention is performed by a biological method. For example, in case of solid phase reaction, it may further include a step of packing immobilized psicose epimerase or microbial cell on a support into a column and a step of providing fructose solution into the packed column. The column being packed by the support-immobilized enzyme or microbial cell and the packing method may be performed according to easily selecting appropriate one by one skilled in the technical field where the present invention belongs according to the used enzyme or microbial cell, or immobilization carrier. In one specific embodiment of the present invention, a packed-bed column may be prepared by packing the immobilized enzyme or microbial cell into a column. An enzymatic reaction, that is, the conversion of fructose to psicose may be performed by providing a substrate of fructose solution to the packed-bed column.

In the conversion reaction of psicose, the reaction may be performed under the condition of pH 4.5 to 7.5, for example, pH 4.7 to 7.0, or pH 5.0 to 6.0 or pH 5.0 to 5.5. In addition, the reaction may be performed under the temperature condition of 30° C. or higher, for example 40° C. or higher. The enzyme activity for converting fructose to psicose (for example, epimerase) can be controlled by a metal ion, and therefore in the production of psicose, the conversion efficiency from fructose to psicose, in the production rate of psicose can be increased, when the metal ion is added. Thus, the composition for producing psicose may further comprise one or more of metal ions selected from the group consisting of copper ion, manganese ion, calcium ion, magnesium ion, zinc ion, nickel ion, cobalt ion, iron ion, aluminum ion, etc.

The detailed technical contents regarding psicose and its preparation method are disclosed in Korean patent publication No. 2014-0021974, Korean patent publication No. 2014-0054997, Korean patent publication No. 2014-0080282, or Korean patent No. 10-1318422.

The fructose as a raw material put into the psicose conversion process according to the present invention may be prepared by a biological method or chemical method, preferably by a biological method. The fructose as a raw material may be provided as a liquid phase raw material, or a powdery raw material such as fructose powder, and in case of fructose syrup, it may be the product obtained in the biological method or chemical preparation method, or one prepared by dissolving fructose powder in a solvent such as water.

In an embodiment of preparing the fructose raw material with a biological method, the fructose may be obtained by performing a fructose isomerization process which isomerizes a glucose-containing raw material with a fructose isomerase or a microbial cell producing the enzyme and separating it through the primary ion purification, high purity chromatography separation process, the secondary ion purification and concentration for the products of fructose isomerization process.

In the method for producing psicose, for effective production of psicose, the concentration of fructose used as a substrate may be 85 w/v % or higher, 90 w/v % or higher, or 95 w/v % or higher, for example, 85 to 99 w/v %, 88 to 99 w/v %, 88 to 99 w/v %, 85 to 87% (w/v), 88 to 90% (w/v), 91 to 93% (w/v), 94 to 99% (w/v) or 97 to 99% (w/v), based on the total reactants. The concentration of fructose may be decided by considering economics of process and solubility of fructose, and the fructose may be used as a solution prepared by dissolving fructose in a buffer solution or water (for example, distilled water).

To illustrate the fructose preparation process according to an example of the present invention, the fructose may be obtained from sugar or glucose. As a result, a method for preparing psicose at high yield by using generalized and inexpensive raw material such as glucose, fructose and sugar is provided, thereby enabling mass production of psicose.

To illustrate one embodiment of fructose preparation process of the present invention, the saccharification solution with 88% by weight or higher of glucose content is obtained by enzymatic hydrolysis, after mixing corn starch with water to be 30 to 35% by weight. Then, by passing a step of removing impurities of the saccharification solution and a fructose isomerization step, a fructose syrup with 40 to 44% by weight of fructose content is obtained. Then, glucose raffinate and fructose fraction are obtained by using a SMB chromatography and are passed through the secondary ion purification and concentration of the fructose fraction are performed, to produce n a fructose-containing solution with 85% by weight or higher, for example 85 to 99% by weight of fructose content. The SMB adsorption separation method is described in the following (2) item. The process for removing impurities may be performed by a step for removing insoluble materials, a step of decoloring by using activated carbon, and a step of passing solution into an ion exchange resin column for removing impurities of colored components and ion components, etc.

A specific embodiment of fructose separation process may comprise the primary ion purification, a high purity chromatography separation, secondary ion purification, a concentration and a crystallization, and optionally carry out desalting, decoloring, or decoloring and desalting process of conversion product.

The concentration step included in the fructose preparation process of the present invention may be conducted with various methods, so as to be fructose content of 85% by weight or higher. For example, the fructose fraction obtained by the SMB adsorption separation method (for example, solid concentration of 20-30%) may be concentrated to be the solid concentration of 45 to 55% by weight through the concentration process.

(2) Separation Process of Psicose-Conversion Product

The psicose preparation method according to the present invention may comprise a separation process of psicose-conversion product, including ion purification and SMB chromatography separation of the psicose-conversion product. In one specific embodiment, SMB chromatography separation to the psicose-conversion product is performed, thereby producing psicose fraction with higher psicose content than the psicose-conversion product and fructose raffinate. The psicose fraction is put into a concentration step or crystallization step and the fructose raffinate is put into a psicose conversion process as a fructose-containing raw material and recycled.

The psicose fraction may be performed in separation/purification so that the psicose content is 85% by weight or higher, for example, 85% by weight to 95% (w/w). The fructose content of fructose raffinate obtained in the high-purity separation process may be 85% by weight or higher, for example 85% by weight to 98% by weight, the psicose content may be preferably 2% by weight or lower. The content of saccharides including disaccharides or higher degree of polymerization other than fructose and glucose in the fructose raffinate may be preferably less than 10% by weight based on the solid content of the total saccharides. The saccharides including disaccharides or higher degree of polymerization in impurities include maltose, isomaltose and etc, and may contain maltose-related or isomaltose-related oligosaccharides.

When the fructose raffinate is recycled for the psicose conversion reaction, the content of impurities is increased as the numbers of recycle are increased. It is preferable to perform the process so that the content of impurities of the fructose raffinate is adjusted below the specific numerical range. When the content of impurities is over the specific numerical range, the impurities are removed by discharging the fructose raffinate partially or overall in the psicose preparation process. For example, it is preferable to maintain the content of saccharides including disaccharides or higher degree of polymerization in the fructose raffinate to less than 10% by weight, for example, less than 8% by weight, less than 6% by weight or lower than 5% by weight, based on 100% by weight of the total saccharide solid of fructose raffinate.

The ion purification step in the psicose preparation process is a process for removing ion comprised in psicose-conversion product, and it may be conducted before and/or after SMB chromatography separation step. The primary ion purification which performs ion purification process before conducting the SMB chromatography separation may be carried out by the same or different method with the following secondary ion purification of psicose fraction. For example, it may be performed by using 1, 2 or more separation columns packed with same kind or different kinds of ion exchange resin. The ion purification process may be performed at 35 to 50° C. temperature, for example, 38 to 58° C., considering physical properties of resin used for ion purification and ion purification efficiency.

In one embodiment of the present invention, before performing the primary ion purification process of psicose-conversion product, a process for treating the psicose-conversion product with activated carbon may be further carried out optionally.

In one embodiment of the present invention, the high purity separation step using SMB chromatography is a separation method useful for securing stability of materials, due to no phase change in the separation process. In these adsorption separation methods, a chromatography separation method has been used in abundance as a liquid phase adsorption separation method. Among them, a simulated moving bed (SMB) adsorption separation method is a separation technology proposed in U.S. Pat. No. 2,985,589 in 1961, and has an advantage that the purity and productivity are excellent and the use of less solvent is possible, compared to the conventional batch chromatography, by continuous separation using many of columns. The simulated moving bed (SMB) adsorption separation process is a process, in which injection of separation target mixture and production of raffinate and extract are implemented continuously.

The fundamental principle of SMB is to copy the flow of immobilized or moving counter-current and enable the continuous separation by moving positions between columns at regular intervals. The material which moves fast due to its weak affinity with an adsorbent moves in the direction of flow of liquid phase and collects in the extract, and the material which moves slowly due to its strong affinity with an adsorbent moves in the direction of flow of immobilized phase and collects in raffinate. Columns are connected continuously, and the inlet consists of mixture and moving phase, and the outlet consists of target extract and raffinate.

Since a cation exchange resin of strong acid in which a salt is added, which is widely used for a process of monosaccharide separation is used as a separation resin in the SMB, metal ions are comprised in products obtained after performing the separation process. An example of cation exchange resin of strong acid may be a cation exchange resin in which a calcium activated group is attached.

Figure 1:
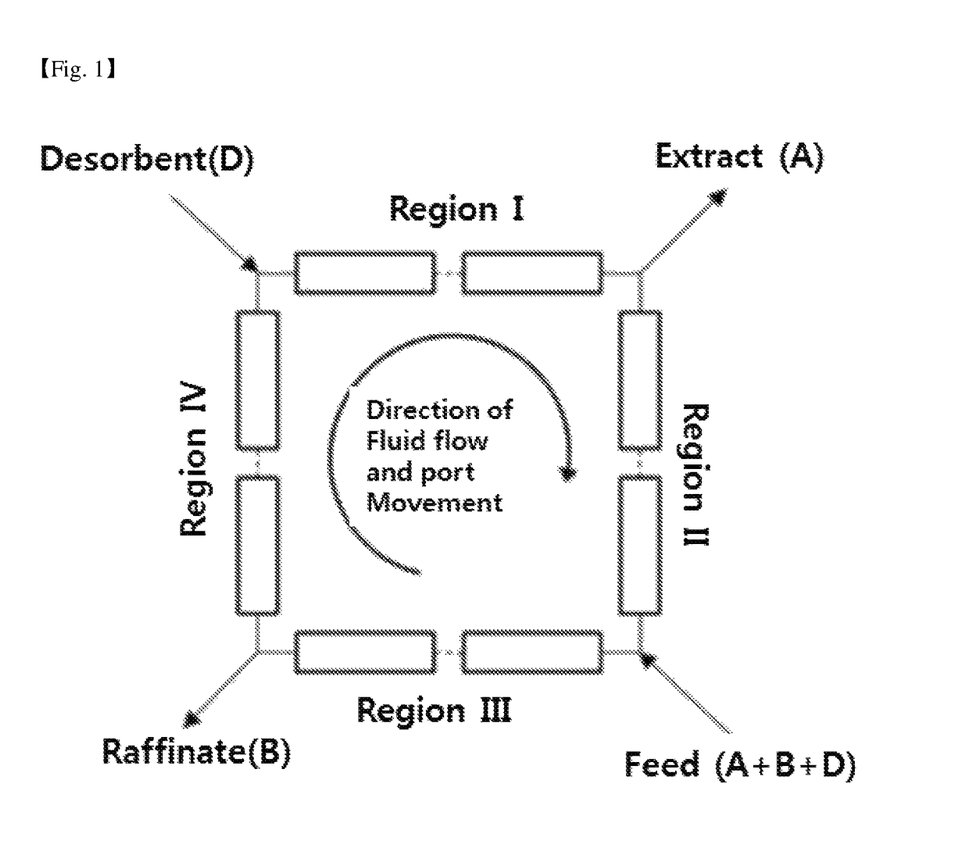
FIG. 1 is a diagram showing one example of general SMB process.
Figure 2:
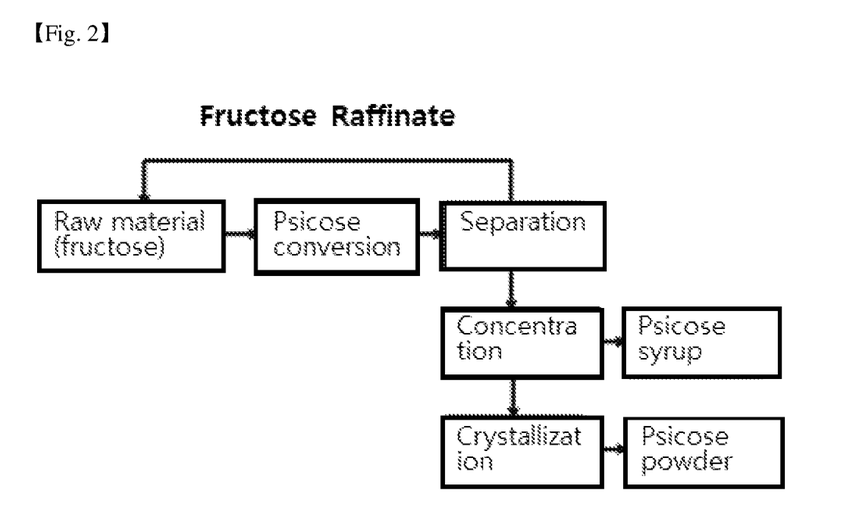
FIG. 2 is a schematic diagram of preparing psicose which entire amount of fructose raffinate is added to the psicose conversion reaction, in accordance with an embodiment of the present invention.
Figure 3:
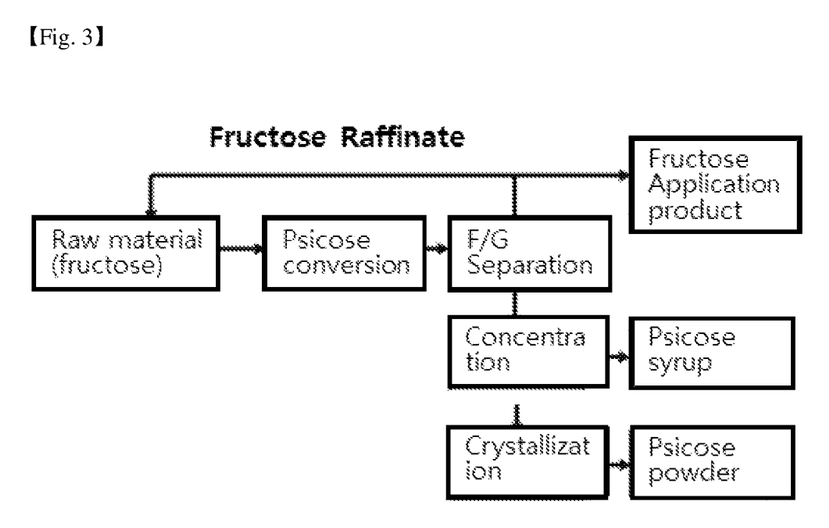
FIG. 3 is a schematic diagram of preparing psicose which a part of fructose raffinate is added to the psicose conversion reaction, in accordance with an embodiment of the present invention.

FIG. 1 shows a process chart of general simulated moving bed (SMB) adsorption separation apparatus. The general simulated moving bed (SMB) adsorption separation apparatus consists of adsorbent inlet port positioned in 4 sections consisting of one or more columns and between each section, an extract discharge port that is a strong absorbate, a separation target mixture (feed) inlet port and a raffinate discharge port that is a weak adsorbate. The separation method of mixture using similar simulated moving bed (SMB) adsorption separation apparatus may be applied for separation of mixture of aromatic hydrocarbons, separation process of ethyl benzene, separation process of chiral compounds, etc, and it may be applied for separation process of racemic mixture drugs which are final products or intermediates in the drug preparation process.

The high purity separation process may be performed at 45 to 70° C. temperature, for example 50 to 65° C.

(3) Recycling of Fructose Raffinate

In the method of preparing psicose according to the present invention, the fructose raffinate obtained in the SMB chromatography separation process is recycled into the psicose conversion reaction as a reactant, thereby increasing the production yield of psicose and lowering the production cost of psicose. When the fructose raffinate obtained in the SMB chromatography separation process is recycled into the psicose conversion reaction, the reduced amount of fructose-containing raw material compared to no recycle of fructose raffinate, thereby decreasing the production load of raw material. In order to continuously produce target product such as psicose through the operation of the psicose production process, the bio-conversion reactor can be operated while maintaining an appropriate level of productivity relative to the initial activity.

Before using the fructose raffinate for the reactant of psicose conversion reaction, it may be performed by cooling, concentrating, ion-purifying, and pH-adjusting so as to be appropriate conditions of the reactant for psicose conversion reaction, and then the processed product can be put to the psicose conversion reaction, by making it to have the properties of the solid content (Brix) equivalent to that of the fresh fructose raw material, pH value (i.e., neutral pH), and reduced concentration of calcium ion.

In one embodiment of the present invention, the fructose raffinate obtained in the high-purity separation process of psicose preparation can be added alone or in combination with the fresh fructose starting material as a reactant for the psicose conversion reaction. When a mixture of the fructose raffinate and the fresh fructose starting material is used as reactant for the psicose conversion reaction, the mixing ratio of the fructose raffinate and the fresh fructose raw material can be appropriately controlled, in order to maximize the utilization of fructose raffinate and to maximize the yield of the psicose obtained in the process. In aspects of the process maintenance, the fresh fructose content can be set to the maximum, but it is not appropriate as the recycling of fructose raffinate. The mixing ratio can be adjusted preferably so as to maximize utilization of fructose raffinate obtained in the high-purity separation process. For example, it is possible to mix the fructose raffinate at an amount of supplement amount as much as the reduced amount, after performing the psicose conversion reaction with the supplied fresh raw material, or to increase the amount of the used fructose raffinate up to the specific value, so as to maintain the yield of the psicose. Further, as the number of recycle of fructose raffinate increases, the content of impurities including disaccharides or higher degree of polymerization and glucose in the fructose raffinate except for fructose increases, the number of recycle and the mixing ratio with fresh fructose raw material can be appropriately adjusted, in order to maintain the content of these impurities to be specific value or less.

The amount of the fresh fructose raw material to be mixed with the fructose raffinate can be determined by considering the biological catalyst such as enzymes, cells, extracts, or lysates, etc., which determines the conversion rate or production yield of converting the fructose starting material to psicose, the conversion rate of biological catalyst, or various factors in the psicose preparation process such as the fructose content. For example, the contents in the fresh fructose raw material and/or the fructose raffinate can determine the amount of the fresh fructose raw material to be mixed. That is, when the fructose content in the fresh fructose raw material is high, the fructose content of the mixture of the fructose raffinate and the fresh fructose raw material increases, so that the amount of the fructose raffinate can be increased compared to the fresh fructose raw material with a low fructose content. The fructose raffinate obtained in the separation process of the present invention may have a fructose content of 85% by weight or higher, for example, 85% by weight to 99% by weight. In addition, the fructose content of the fresh fructose raw material put into the psicose conversion reaction may be 85% by weight or higher, for example, 85% by weight to 99% by weight.

When the mixture of the fructose raffinate and the fresh fructose raw material is used as a reactant for the psicose conversion reaction, the amount of the fresh fructose rat material to be mixed with the fructose raffinate can be determined in consideration of the various factors as described above. It can be determined appropriately in consideration of the fructose content, Brix, operation mode of the psicose production system, yield and the like. Considering the utilization of fructose raffinate obtained in the separation process of psicose preparation, all the fructose raffinate may be used as a reactant with supplementing the fresh fructose raw material at an amount of reduced fructose raw material. A part of the fructose raffinate may also be used as a fructose raw material in the psicose conversion system, which the psicose preparation system is operated only with the fresh fructose raw material. Therefore, the fructose raffinate may be used as a whole, or used at a minimal amount and the remaining amount may be discharged from the system. Thus, the amount of fructose raffinate introduced into the psicose conversion reaction can be recycled with the maximum content of all the fructose raffinate obtained in the separation process, as long as system operation is allowed.

Specifically, considering the maximum utilization of fructose raffinate, it is preferable to use all of the fructose raffinates. In this case, it is possible to supplement the deficiency of the reduced fructose source by the fresh fructose raw material. For example, when the fructose raffinate and the fresh fructose raw material are adjusted to 50 Brix, the volume ratio of the new fructose raw material may be 5 to 150 parts by volume, or preferably 50 to 130 parts by volume, based on 100 parts by volume of fresh fructose raw material. For example, when the fructose raffinate and the new fructose raw material are adjusted to 50 Brix, the mixing ratio of the fructose raffinate and the new fructose raw material (=fructose raffinate:the new fructose raw material) may be 1:0.9 to 1.5 of volume ratio. The mixing ratio may vary depending on the fructose concentration of the new fructose raw material. For example, when the fructose raffinate and the fresh fructose raw material are adjusted to 50 Brix, the mixing ratio of the fructose raffinate and the fresh fructose raw material is 1:0.9 to 1.5 of volume ratio, 1:0.95 to 1.15 of volume ratio, or 1:0.98 to 1.05 of volume ratio volume ratio, and the mixing ratio of fructose raffinate:the fresh fructose raw material may be 1:1.05 to 1.2 or 1:1.08 to 1.13 of volume ratio.

When the addition amount of the fresh fructose raw material to the fructose raffinate is less than the range, the fructose purity of the raffinate introduced into the psicose conversion reaction decreases as the number of recycle of the fructose raffinate increases, thereby decreasing the psicose conversion rate and the final production yield of psicose. Therefore, by considering the production time and the psicose yield, the process should be optimized so as to maintain an appropriate production yield of the psicose. When the mixing ratio satisfies the range condition, the psicose conversion process may be continued to maintain the fructose purity of the starting material provided into the psicose conversion process within an appropriate range, and the conversion rate of the psicose can be stably maintained.

In an embodiment of the present invention, the recycle of fructose raffinate increases the calcium content, thereby lowering the activity of the psicose conversion reaction. Thus, it is preferable to use a process for controlling the calcium ion concentration. The step of adjusting the ion concentration can be performed using chromatography packed with an ion exchange resin. Specifically, an ion exchange process using a strongly basic or weakly basic anion resin substituted with a hydroxy group (OH—) capable of binding a metal ion can be performed.

The calcium ion concentration of the fructose raffinate or the fructose-containing raw material including the fructose raffinate, the may be adjusted to be 0.01 mM or lower, 0.005 mM or lower, or 0.001 mM or lower, before providing the fructose raffinate into the psicose conversion reaction. In the reuse of fructose raffinate produced in the SMB chromatography process, when the calcium (Ca) ion mixed in the SMB chromatography process is not purified, the activity is lowered than use of only manganese, thereby doing bad influence on the psicose production amount.

Since the cation exchange resin of the strong acid which is widely used in the separation process of the monosaccharide is used in the SMB high-purity separation process of the psicose conversion product, a part of calcium attached to the resin flows out as it is used, the product obtained after the process includes calcium ions. In particular, excessive amount of calcium ions adversely affects the psicose conversion. Therefore, the fructose raffinate is required for adjusting the calcium ion concentration to a specific concentration range or less. This is also related to the durability of the resin. As the viscous saccharide solution passes, the friction due to the viscosity is generated, and the metal ions attached to the resin surface are discharged in small amounts. For this reason, in case that the ion exchange resin is used for a long time after packing, the resin is replaced at regular intervals.

The ion purification of the fructose raffinate can be carried out in the same method as the ion purification performed in the step of separating the psicose conversion product of item (2).

The fructose raffinate obtained in the chromatography separation process has an electric conductivity of 20 to 200 µs/cm, the fructose raffinate can be treated by an ion purification process, and the treated product has an electric conductivity of 0 to 15 µs/cm.

In one embodiment of the present invention, the fructose raffinate obtained in the separation process of the psicose preparation may be further subjected to a step of increasing the fructose content by concentrating with or after ion purification. When the fructose raffinate obtained in the high-purity separation process of the psicose preparation has a low brix, the concentration process can be performed to adjust the solid content so as to become the same or similar brix as the fresh fructose raw material. Because the fructose raffinate obtained in the high-purity separation process of psicose preparation is about 15 to 25 Brix, the fructose content may be increased by concentrating, in consideration that the fructose-containing raw material supplied to the psicose conversion process is usually 45-55 Brix, for example, about 50 Brix, To increase the fructose content.

The concentration step is carried out in the same manner as the concentration step used in the fructose preparation for producing fructose raw material by performing fructose isomerization from glucose as a raw material or in the same manner as the concentration step of the psicose fraction obtained after SMB high-purity separation. The concentration step in the fructose production may include concentrating for 10 to 15 minutes at a temperature of 70 to 85° C., because the heat stability of fructose is higher than that of psicose.

In a specific example of the present invention, before providing the fructose raffinate obtained in the separation step of the psicose preparation into the psicose conversion process, the ion purification step and/or the fructose condensation step is carried out by using a separate device.

The method of preparing psicose further includes the steps of treating the fructose with at least step selected from the group consisting of cooling, concentration, ion purification and pH adjustment and putting to a storage tank, adjusting the temperature, or controlling the amount of fructose raffinate added to the psicose conversion process.

(4) Psicose Concentration or Crystallization Process

The psicose fraction obtained in the high-purity separation process using SMB chromatography in the psicose preparation process of the present invention may be commercialized as liquid phase syrup through a psicose concentration process, or may be commercialized as psicose crystals through a psicose crystallization process.

It is a step of preparing concentrates obtained by ion purifying and concentrating psicose fraction obtained in the SMB chromatography separation of the step (2). The concentrates may be used as a psicose syrup product or prepared for psicose crystals by putting into a crystallization process.

In one embodiment of the present invention, the secondary ion purification of psicose fraction obtained in the high purity separation process using SMB chromatography may be performed, and it may be performed by the same or different methods with the primary ion purification performed in the separation process.

The psicose content in the psicose solution for collecting psicose crystals should be contained at a high concentration in the supersaturation condition, but the psicose content of psicose conversion product is low, so direct crystallization for psicose conversion product cannot be conducted and a process of purification and concentration up to the desired level should be performed to increase the psicose content before the crystallization step.

In one specific embodiment of the present invention, the step of concentrating purified psicose solution may be performed at 55 to 75° C. When the temperature of concentrated solution is increased over 75° C., thermal modification of D-psicose may occur, and when decreased less than 55° C., desired level of concentration is difficult to achieve. Since the temperature of product is rapidly increased by evaporation heat as the concentration progresses, it should be concentrated rapidly by maintaining the temperature of concentrated solution to 75 or less.

In one specific embodiment of the present invention, in order to achieve thermal modification of psicose and desired level of concentration, it may be concentrated in the range of 55 to 75° C. temperature, preferably 60 to 70° C. The concentration process may be conducted once or twice or more repeatedly until achieving the desired concentration level.

Specifically, the concentration process of psicose fraction obtained in the SMB chromatography separation process may be performed by various methods, and the solid content in the concentrates may be 70 Brix or higher. For example, the psicose fraction obtained by the SMB adsorption separation method (for example, solid content 20-30% by weight) may be concentrated to the solid content of 70 Brix or higher through the concentration process. The solid content in the psicose concentrates may be 70 Brix or higher, for example, 70 Brix to 85 Brix.

The concentration process in the psicose preparation process may comprise concentrating in the temperature range of 55 to 75° C. for 10 to 15 min. The concentration may concentrate under decompressed or vacuumed conditions by using a falling film evaporator or thin film evaporator.

The psicose content comprised in the psicose concentrates is almost same as psicose content of psicose fraction obtained in the SMB chromatography separation process, and the solid content is increased, thereby enabling the crystallization process to perform. The psicose content comprised in the psicose concentrates may be 94% by weight or higher, 95% by weight or higher, 96% by weight or higher, 97% by weight or higher, 98% by weight or higher, or 99% by weight or higher, based 100% by weight of the solid total content.

The psicose crystallization process comprises a step of secondary ion purification of psicose fraction obtained in the high-purity separation, a step of concentrating the ion-purified psicose fraction, and a step of obtaining psicose crystals and psicose crystallization mother liquor by crystallizing psicose from the concentrates. A specific example of the psicose separation process may include the primary ion purification, high-purity chromatography separation, the secondary ion purification, concentration and crystallization processes, and optionally, may carry out desalting process, decoloring or decoloring and desalting process of psicose conversion product.

It may comprise separation/purification so that the content of psicose in the psicose fraction is 85% by weight or higher, 90% by weight or higher, 91% by weight or higher, 92% by weight or higher, 93% by weight or higher, 94% by weight or higher, or 95% by weight or higher, for example, 85% by weight to 99.9% (w/w).

The psicose purity contained in the psicose crystals may be 90% by weight or higher, 95% by weight or higher, or 99% by weight or higher, and the psicose content in the crystallization mother liquor may be 85% by weight or higher, 90% by weight or higher, 93% by weight or higher, or 95% by weight or higher, for example, 85% by weight to 95% by weight.

The psicose collected by the method of the present invention may be purified and/or crystallized by common methods, and these purification and crystallization belong to common technologies to one skilled in the art. For example, it may be implemented by one or more methods selected from the group consisting of centrifugation, filtration, crystallization, ion exchange chromatography and combinations thereof.

In one embodiment, the secondary ion purification may be conducted for the psicose fraction obtained in the high purity separation process using SMB chromatography, and it may be carried out by the same or different methods with the primary ion purification used in the separation process of psicose.

The method for preparing D-psicose crystals according to the present invention may comprise a step of concentrating purified D-psicose solution. The content of psicose in the psicose solution for collecting psicose crystals should be 70% by weight or higher. The purity of psicose in the psicose solution prepared by the psicose epimerase is low as 20 to 30% by weight, so direct crystallization cannot be conducted and a process of purification and concentration up to the desired level should be performed to increase the content of psicose before the crystallization step. In one specific embodiment of the present invention, in order to achieve thermal modification of psicose and desired level of concentration, the concentration may be implemented in the temperature range of 55 to 75° C. The concentration process may be conducted once or twice or more repeatedly until achieving the desired concentration level.

The step of crystallization by cooling may comprise inducing crystal growth by repeatedly conducting temperature rising and cooling, after rapidly cooling in the temperature range of 10 to 25° C. through a heat exchanger.

The method for preparing D-psicose crystals according to the present invention may further comprise a step of drying after recovering psicose crystals collected in the crystallization step by centrifugation and washing it with deionized water.

One embodiment according to the present invention relates to an apparatus of preparation of psicose by performing psicose conversion reaction and psicose separation process, comprising a psicose conversion reactor for performing psicose conversion reaction from fructose-containing raw material,
    an ion purifier equipped with a column packed with ion exchange resin which ion purifies psicose conversion product obtained from the psicose conversion reactor,
    a simulated moving bed (SMB) chromatography separator which comprises a column packed with cation exchange resin having an active group, a feed inlet and an outlet for discharging psicose fraction and fructose raffinate, an ion purifier equipped with a column packed with ion exchange resin and a concentrator, wherein the fructose raffinate discharged from the separator is performed for ion purification and concentration, so as to recycle into the psicose conversion reactor.

The psicose preparation apparatus may further include a mixing vessel connected to the psicose conversion reactor and configured to mix the fructose raffinate discharged from the concentrator with the fresh fructose raw material. The apparatus may further include a heat exchanger for cooling the fructose raffinate discharged from the chromatographic separator.

Effect of the Invention

The use of fructose raffinate according to the present invention can produce an effective production of psicose and liquid fructose. Particularly, it is possible to control the mixing ratio of fructose raffinate and new fructose raw material to prevent the quality of the liquid fructose raw material being deteriorated, and to maintain the fructose content of fructose syrup with high fructose content, thereby producing psicose with a stably high yield over a long period of time.

DETAILED DESCRIPTION OF THE EMBODIMENTS

Hereinafter, the present invention will be described in more detail with the following examples. However, these examples are only for illustrative purpose, and the scope of the present invention is not limited by these examples.'

Preparative Example 1. Preparation of Psicose Syrup

A psicose syrup was prepared from a fructose substrate by the biological method substantially same with the preparation method disclosed in the Korean laid-open patent publication No. 2014-0054997.

Specifically, the encoding gene of psicose epimerase derived from *Clostridium scindens* (*Clostridium scindens* ATCC 35704) (DPE gene; Gene bank: EDS06411.1) was introduced into a recombinant vector (pCES_sodCDPE), and *Corynebacterium glutamicum* was transformed by using the prepared recombinant vector (pCES_sodCDPE) plasmid with electroporation. A bead including the transformed *Corynebacterium glutamicum* cell was prepared and packed into an immobilization reaction column, and a psicose syrup was prepared from 40 brix of 88% by weight of fructose or 95% by weight of fructose. That is, the psicose syrup of 21~23 (w/w) % of which weight ratio of glucose:fructose:psicose:oligosaccharide is 41:39:15:5 from 88% by weight of fructose-containing substrate (psicose syrup A), and the psicose syrup of 24~26 (w/w) % of which glucose:fructose: psicose:oligosaccharide=6:67:25:2 from the raw material comprising 95% by weight of fructose content (psicose syrup B).

Preparative Example 2. Preparation of Fructose Raffinate

Two kinds of psicose syrups obtained from Preparative Example 1 were flew through the column at a room temperature which was packed with resin in which cation exchange resin, anion exchange resin and cation and anion exchange resin mixed resin at a rate of twice the volume of ion exchange resin per hour and desalted in order to remove impurities such as colored and ion components, etc.

Then, after separating high purity of psicose fraction by using a chromatography packed with calcium ($Ca^{2+}$) type of ion exchange resin, the remainder was collected as raffinate. The raffinate collected from the psicose syrup obtained from the raw material of 77% by weight of fructose content (psicose syrup A) included 85 to 98% by weight of fructose, 1 to 10% by weight of glucose, and 1 to 5% by weight of reducing sugar, based on 100 parts by weight of the total solid content of saccharides.

The raffinate collected from the psicose syrup obtained from the raw material of 95% by weight of fructose content (psicose syrup B) included 88 to 98% by weight of fructose, 1 to 8% by weight of glucose, and 1 to 4% by weight of reducing sugar r, based on 100 parts by weight of the total solid content of saccharides.

Example 1. Production of Psicose Using Fructose Raffinate

To produce 10 tons of solids of 95% by weight of psicose content by using the fructose-containing raw material solution of 88% by weight of fructose content obtained in Preparative Examples 1 and 2, the psicose conversion process and separation process were carried out at flow rate 3.8 $m^3$/hr.

The psicose content of product collected through the psicose conversion process was 20 to 23% by weight, and they passed through the separation process at a concentration of 45 to 50% by weight after ion purification. The raffinate which was generated when separated by using Ca+ type separation (SMB) resin was generated by 3 $m^3$ per hour.

Specifically, the psicose syrup with psicose content of 20 to 23 wt % was obtained through the psicose conversion process with a raw substrate solution (psicose syrup A) having a fructose content of 88 wt %. The psicose conversion product was desalted by passing through a column packed with a cation exchange resin, a column packed with an anion-exchange resin and a column packed with a mixture of a cation and an anion-exchange resin at a speed rate of 2 times (1 to 2 times) by volume based on the rate of ion exchange resin at room temperature. Then, the product was concentrated to produce psicose syrup with the psicose content of 45 to 50% by weight. The psicose syrup was passed through the SMB high-purity chromatography with $Ca^{2+}$-type separation resin to produce the fructose raffinate at 3.1 $m^3$ per hour.

The deficient amount of fructose, 0.9 $m^3$ in the psicose conversion process and the SMB chromatography was supplemented with the fructose-containing raw material of 88% by weight of fructose content obtained in fructose preparation process. That is, when the total solid content of the fresh fructose raw material and fructose raffinate were adjusted to 50 wt % (Brix), a mixture of the fresh fructose raw material and the fructose raffinate mixed in a volume ratio of 0.9:3.1 (fresh fructose:fructose raffinate=0.29:1) was added to the psicose conversion process to perform the psicose preparation process.

The process was repeated 10 times, and the saccharide composition of the mixed raw materials and raffinate according to each process was analyzed and shown in Table 1 below.

TABLE 1

| Classification | Saccharide including disaccharides or higher degree of polymerization | Glucose | Fructose | Psicose | Reducing sugar | Psicose yield |
|---|---|---|---|---|---|---|
| F88 raw material | 1.1% | 5.0% | 88.1% | 0.0% | 5.8% | 22.9% |
| raffinate | 1.5% | 8.3% | 85.6% | 0.3% | 4.3% | |
| 1st mixture solution | 1.4% | 7.8% | 86.2% | 0.2% | 4.4% | 22.4% |
| 1st raffinate | 1.8% | 9.4% | 83.0% | 0.3% | 5.3% | |
| 2nd mixture solution | 1.4% | 7.1% | 85.7% | 0.1% | 5.6% | 22.3% |
| 2nd raffinate | 1.7% | 8.6% | 82.5% | 0.2% | 6.8% | |
| 3rd mixture solution | 1.6% | 8.2% | 84.4% | 0.2% | 5.5% | 21.9% |
| 3rd raffinate | 1.9% | 9.9% | 80.9% | 0.3% | 6.7% | |
| 4th mixture solution | 1.7% | 8.5% | 83.4% | 0.2% | 6.1% | 21.7% |
| 4th raffinate | 2.0% | 10.3% | 79.7% | 0.2% | 7.4% | |
| 5th mixture solution | 1.8% | 9.2% | 82.2% | 0.2% | 6.4% | 21.4% |
| 5th raffinate | 2.2% | 11.2% | 78.2% | 0.3% | 7.8% | |
| 6th mixture solution | 1.9% | 9.7% | 80.9% | 0.2% | 6.9% | 21.0% |
| 6th raffinate | 2.3% | 11.8% | 76.7% | 0.3% | 8.4% | |
| 7th mixture solution | 2.0% | 10.4% | 79.6% | 0.2% | 7.4% | 20.7% |
| 7th raffinate | 2.5% | 12.7% | 75.0% | 0.3% | 9.0% | |
| 8th mixture solution | 2.2% | 11.1% | 78.1% | 0.3% | 7.9% | 20.3% |
| 8th raffinate | 2.6% | 13.5% | 73.3% | 0.3% | 9.6% | |
| 9th mixture solution | 2.3% | 11.9% | 76.6% | 0.3% | 8.4% | 19.9% |
| 9th raffinate | 2.8% | 14.5% | 71.4% | 0.3% | 10.2% | |
| 10th mixture solution | 2.5% | 12.7% | 75.0% | 0.3% | 9.0% | 19.5% |
| 10th raffinate | 3.0% | 15.5% | 69.4% | 0.4% | 10.9% | |

As can be seen in the Table 1, it was demonstrated that the mixing ratio of the fresh fructose raw material and the fructose raffinate was in a volume ratio of 0.9:3.1 (fresh fructose:fructose raffinate=0.29:1), the psicose conversion rate and the final psicose yield were reduced due to the fructose purity of fructose raffinate put to the psicose conversion process, as the number of recycle increased.

Example 2. Production of Fructose Using Fructose Raffinate 1.8 m³/hr of fructose raffinate obtained in the high-purity separation step was mixed with 2.0 m³/hr of fresh fructose raw material (fructose purity: 88 wt %, solid concentration: 50 wt %) and supplied to the ion purification step. The mixing ratio of the fresh fructose raw material and the fructose raffinate were 5.2 to 5.3:4.7 to 4.8 (fresh ructose:fructose raffinate=1.08 to 1.13:1).

The process was repeated 10 times, and the saccharide composition of the mixed raw materials and raffinate according to each process was analyzed and shown in Table 2 below.

TABLE 2

| Classification | Saccharide including disaccharides or higher degree of polymerization | Glucose | Fructose | Psicose | Reducing sugar | Psicose yield |
|---|---|---|---|---|---|---|
| F88 raw material | 1.1% | 5.0% | 88.1% | 0.0% | 5.8% | 22.9% |
| raffinate | 1.5% | 8.3% | 85.6% | 0.3% | 4.3% | |
| 1st mixture solution | 1.3% | 6.6% | 86.9% | 0.1% | 5.1% | 22.6% |
| 1st raffinate | 1.6% | 8.0% | 84.0% | 0.2% | 6.2% | |
| 2nd mixture solution | 1.3% | 6.4% | 86.1% | 0.1% | 6.0% | 22.4% |
| 2nd raffinate | 1.6% | 7.8% | 83.0% | 0.1% | 7.3% | |
| 3rd mixture solution | 1.3% | 6.3% | 85.7% | 0.0% | 6.5% | 21.9% |
| 3rd raffinate | 1.6% | 7.7% | 82.5% | 0.1% | 7.9% | |
| 4th mixture solution | 1.4% | 6.3% | 85.4% | 0.0% | 6.8% | 21.9% |
| 4th raffinate | 1.6% | 7.6% | 82.1% | 0.0% | 8.3% | |
| 5th mixture solution | 1.4% | 6.3% | 85.3% | 0.0% | 7.0% | 21.5% |
| 5th raffinate | 1.7% | 7.6% | 82.0% | 0.0% | 8.5% | |
| 6th mixture solution | 1.4% | 6.2% | 85.2% | 0.0% | 7.1% | 21.5% |
| 6th raffinate | 1.7% | 7.6% | 81.9% | 0.0% | 8.6% | |
| 7th mixture solution | 1.4% | 6.2% | 85.1% | 0.0% | 7.1% | 21.5% |
| 7th raffinate | 1.7% | 7.6% | 81.8% | 0.0% | 8.7% | |
| 8th mixture solution | 1.4% | 6.2% | 85.1% | 0.0% | 7.2% | 21.5% |
| 8th raffinate | 1.7% | 7.6% | 81.8% | 0.0% | 8.7% | |
| 9th mixture solution | 1.4% | 6.2% | 85.1% | 0.0% | 7.2% | 21.5% |
| 9th raffinate | 1.7% | 7.6% | 81.7% | 0.0% | 8.7% | |
| 10th mixture solution | 1.4% | 6.2% | 85.1% | 0.0% | 7.2% | 21.5% |
| 10th raffinate | 1.7% | 7.6% | 81.7% | 0.0% | 8.7% | |

As can be seen in the Table 2, it was demonstrated that the mixing ratio of the fresh fructose raw material and the fructose raffinate was in a volume ratio of 5.2 to 5.3:4.7 to 4.8 (fresh fructose:fructose raffinate=1.08 to 1.13:1), even if the psicose conversion process was continuously performed, the fructose purity of fructose raffinate put to the psicose conversion process was not reduced significantly and the psicose conversion rate was maintained stably from the 5$^{th}$ mixture.

TABLE 3

| Classification | Saccharide including disaccharides or higher degree of polymerization | Glucose | Fructose | Psicose | Reducing sugar | Psicose yield |
|---|---|---|---|---|---|---|
| Fructose reactant | 1.1% | 5.0% | 88.1% | 0.0% | 5.8% | 1.1% |
| Psicose conversion product | 1.1% | 5.0% | 65.2% | 22.9% | 5.8% | 1.1% |
| Product after purification/concentration | 1.1% | 5.0% | 65.2% | 22.9% | 5.8% | 1.1% |
| Psicose fraction after high-purity separation | 0.0% | 0.0% | 1.8% | 97.2% | 1.0% | 0.0% |
| Fructose raffinate after high-purity separation | 1.5% | 8.3% | 85.6% | 0.3% | 4.3% | 1.5% |
| Fructose syrup (55%) | 2.4% | 39.5% | 56.5% | 0.0% | 1.6% | 2.4% |
| Product after purification/concentration of psicose fraction | 0.0% | 0.0% | 1.8% | 97.2% | 1.0% | 0.0% |
| Psicose crystal | 0.0% | 0.0% | 0.1% | 99.9% | 0.0% | 0.0% |
| Psicose crystallization mother liquor | 0.0% | 0.0% | 7.6% | 89.5% | 2.9% | 0.0% |

As shown in Table 3, when the psicose conversion process was operated by using the fructose raw material with fructose purity of 88% by weight, the psicose conversion rate was about 23% and the psicose syrup with psicose purity of 95 wt % or higher was obtained by the high-purity separation process. At this time, the separation yield of psicose was the psicose content of 90 wt % or higher The separated high-purity psicose fraction can be purified as a liquid product or subjected to a crystallization process to produce a crystallized product having a psicose content of 99.9% by weight. When the crystallization process was carried out, As shown in Table 3, the psicose content was 95% by weight or higher. The fructose raffinate obtained after high purity separation process was concentrated to a solid content of 50 to 77 wt % and mixed with fresh fructose raw material having a fructose content of 42 wt % (solid content 50 to 77 wt %) to obtain a liquid fructose syrup having a purity of 56.5 wt %.

Example 3. Production of Psicose Using Fructose Raffinate

The psicose conversion process and separation process were carried out with the same method as Example 1, but at flow rate of 3.8 m$^3$/hr, in order to produce 10 tons of solids of 95% by weight of psicose content using syrup of 95% by weight of fructose content.

The psicose content of products which were passed through the psicose conversion process and collected was 21 to 25% by weight, and they passed through the separation process at a concentration of 45 to 50% by weight after ion purification. The raffinate which was generated when separated by using Ca+ type separation resin was generated by 3 m$^3$ per hour.

0.8 m$^3$/hr of fructose raw material which was deficient in the psicose conversion process and separation chromatograph was supplied and mixed with the fresh fructose raw material obtained from the fructose preparation process. That is, when the new fructose raw material and the fructose raffinate were adjusted to 50 Brix, the psicose production was carried out with a mixed volume ratio of the new fructose raw material and fructose raffinate of 0.9:3.1 (new fructose raw material:raffinate=0.29:1).

The process was repeated 10 times, and the saccharide composition of the mixed raw materials and raffinate according to each process was analyzed and shown in Table 4 below.

TABLE 4

| Classification | Saccharide including disaccharides or higher degree of polymerization | Glucose | Fructose | Psicose | Reducing sugar | Psicose yield |
|---|---|---|---|---|---|---|
| F95 raw material | 0.1% | 3.5% | 95.2% | 0.0% | 1.2% | 27.1% |
| raffinate | 0.1% | 3.9% | 94.2% | 1.2% | 0.6% | |
| 1st mixture solution | 0.1% | 3.6% | 94.8% | 0.7% | 0.8% | 27.2% |
| 1st raffinate | 0.1% | 3.8% | 94.2% | 1.4% | 0.5% | |
| 2nd mixture solution | 0.1% | 3.6% | 94.6% | 0.8% | 0.9% | 27.1% |
| 2nd raffinate | 0.1% | 3.8% | 94.3% | 1.3% | 0.5% | |
| 3rd mixture solution | 0.1% | 3.6% | 94.5% | 1.1% | 0.7% | 27.1% |
| 3rd raffinate | 0.1% | 3.8% | 94.3% | 1.5% | 0.3% | |

TABLE 4-continued

| Classification | Saccharide including disaccharides or higher degree of polymerization | Glucose | Fructose | Psicose | Reducing sugar | Psicose yield |
|---|---|---|---|---|---|---|
| 4th mixture solution | 0.1% | 3.7% | 94.8% | 0.8% | 0.6% | 27.0% |
| 4th raffinate | 0.1% | 3.9% | 94.4% | 1.3% | 0.3% | |
| 5th mixture solution | 0.1% | 3.7% | 94.8% | 0.7% | 0.7% | 27.0% |
| 5th raffinate | 0.1% | 3.9% | 94.3% | 1.5% | 0.2% | |
| 6th mixture solution | 0.1% | 3.7% | 94.7% | 0.6% | 0.9% | 27.0% |
| 6th raffinate | 0.1% | 3.9% | 94.3% | 1.1% | 0.6% | |
| 7th mixture solution | 0.1% | 3.7% | 94.8% | 0.6% | 0.8% | 26.9% |
| 7th raffinate | 0.1% | 3.9% | 94.2% | 1.3% | 0.5% | |
| 8th mixture solution | 0.1% | 3.7% | 94.7% | 0.8% | 0.7% | 26.9% |
| 8th raffinate | 0.1% | 3.9% | 94.3% | 1.3% | 0.4% | |
| 9th mixture solution | 0.1% | 3.7% | 94.8% | 0.8% | 0.6% | 26.9% |
| 9th raffinate | 0.1% | 3.9% | 94.2% | 1.4% | 0.4% | |
| 10th mixture solution | 0.1% | 3.7% | 94.8% | 0.8% | 0.6% | 26.9% |
| 10th raffinate | 0.1% | 3.9% | 94.2% | 1.5% | 0.3% | |

As can be seen in the Table 4, when psicose was produced using 95% by weight of fructose purity, it was confirmed that the content of fructose was not changed unlike in Example 1. The fructose raw material with the fructose purity higher than 95% by weight supplied into the psicose conversion process was not changed so as to maintain the final psicose production, as the number of recycle of the fructose raffinate increased. It was confirmed that the contents of glucose and disaccharide were not high and the content of fructose was maintained, as a part of reducing sugar was moved into the psicose fraction. These results indicate that the fructose raffinate can be recycled with a high conversion rate of psicose under high purity condition of 95% or higher of fructose content in the fructose raw materials.

Example 4. Continuous Production of Psicose Using Fructose Raffinate

The same method of Example 3 was carried out except that 1.9 m$^3$/hr of fructose raffinate remaining after mixing with 42% of fructose were mixed with 1.9 m$^3$/hr of fresh fructose raw material and then supplied to the psicose conversion process and the chromatography separation process. When the fresh fructose raw material and the raffinate were adjusted to 50 brix, the mixing ratio of the fresh fructose raw material and the fructose raffinate was 5.0 to 5.1:4.9 to 5.1 (fructose raffinate:fresh fructose raw material=1:0.98 to 1.05).

The process was repeated 10 times, and the saccharide composition of the mixed raw materials and raffinate according to each process was analyzed and shown in Table 5 below.

TABLE 5

| Classification | Saccharide including disaccharides or higher degree of polymerization | Glucose | Fructose | Psicose | Reducing sugar | Psicose yield |
|---|---|---|---|---|---|---|
| F95 raw material | 0.1% | 3.5% | 95.1% | 0.0% | 1.3% | 27.2% |
| raffinate | 0.1% | 3.8% | 94.2% | 1.1% | 0.8% | |
| 1st mixture solution | 0.1% | 3.6% | 94.9% | 0.3% | 1.1% | 27.1% |
| 1st raffinate | 0.1% | 3.9% | 94.1% | 1.2% | 0.7% | |
| 2nd mixture solution | 0.1% | 3.6% | 94.8% | 0.5% | 1.0% | 27.1% |
| 2nd raffinate | 0.1% | 3.8% | 94.2% | 1.3% | 0.6% | |
| 3rd mixture solution | 0.1% | 3.6% | 94.9% | 0.4% | 1.0% | 27.1% |
| 3rd raffinate | 0.1% | 3.8% | 94.2% | 1.2% | 0.7% | |
| 4th mixture solution | 0.1% | 3.6% | 94.7% | 0.5% | 1.1% | 27.1% |
| 4th raffinate | 0.1% | 3.7% | 94.2% | 1.2% | 0.7% | |
| 5th mixture solution | 0.1% | 3.6% | 94.7% | 0.4% | 1.2% | 27.0% |
| 5th raffinate | 0.1% | 3.9% | 94.1% | 1.3% | 0.6% | |
| 6th mixture solution | 0.1% | 3.6% | 94.7% | 0.5% | 1.1% | 27.0% |
| 6th raffinate | 0.1% | 3.8% | 94.2% | 1.2% | 0.7% | |
| 7th mixture solution | 0.1% | 3.6% | 94.8% | 0.5% | 1.0% | 27.0% |
| 7th raffinate | 0.1% | 3.8% | 94.1% | 1.3% | 0.7% | |
| 8th mixture solution | 0.1% | 3.6% | 94.8% | 0.5% | 1.0% | 27.0% |
| 8th raffinate | 0.1% | 3.8% | 94.2% | 1.3% | 0.6% | |
| 9th mixture solution | 0.1% | 3.6% | 94.8% | 0.4% | 1.1% | 27.1% |
| 9th raffinate | 0.1% | 3.9% | 94.1% | 1.3% | 0.6% | |
| 10th mixture solution | 0.1% | 3.5% | 94.9% | 0.5% | 1.0% | 27.0% |
| 10th raffinate | 0.1% | 3.8% | 94.2% | 1.2% | 0.7% | |

As shown in Table 5, a portion of the fructose raffinate was used as 55 wt % fructose syrup, and other portion of the fructose raffinate was supplied to the psicose conversion process with mixing with the fresh fructose raw material, thereby stably producing the psicose with high purity. The saccharide composition of the mixed raw materials and raffinate according to each process was analyzed and shown in Table 6.

TABLE 6

| Classification | Saccharide including disaccharides or higher degree of polymerization | Glucose | Fructose | Psicose | Reducing sugar | Psicose yield |
|---|---|---|---|---|---|---|
| Fructose reactant | 0.1% | 3.5% | 95.2% | 0.0% | 1.2% | 0.1% |
| Psicose conversion product | 0.1% | 3.5% | 68.1% | 27.1% | 1.2% | 0.1% |
| Product after purification/concentration | 0.1% | 3.5% | 68.1% | 27.1% | 1.2% | 0.1% |
| Psicose fraction afterhigh-purity separation | 0.0% | 0.0% | 1.5% | 97.6% | 0.9% | 0.0% |
| Fructose raffinate after high-purity separation | 0.1% | 3.9% | 94.2% | 1.2% | 0.6% | 0.1% |
| Fructose syrup (55%) | 2.1% | 39.9% | 56.2% | 0.3% | 1.5% | 2.1% |
| Product after purification/concentration of psicose fraction | 0.0% | 0.0% | 1.5% | 97.5% | 1.0% | 0.0% |
| Psicose crystal | 0.0% | 0.0% | 0.1% | 99.9% | 0.0% | 0.0% |
| Psicose crystallization mother liquor | 0.0% | 0.0% | 6.8% | 90.6% | 2.6% | 0.0% |

As shown in Table 6, even if the part of fructose raffinate was supplied to liquid fructose production process, the psicose production could be stably maintained.

The separated psicose with high-purity can be released as a liquid product through purification or a crystallization process can be performed to produce a crystallized product having a psicose content of 99.9% in the same manner as Example 3. Other matters were the same as in Example 3. When the crystallization process was carried out, as shown in Table 6, the psicose content was 99.9%. Liquid fructose (55% syrup) was obtained as being equitable to the product quality of product obtained by mixing 95% and 42% of liquid fructose.

Example 5. Comparative Experiment of Psicose Conversion Ratio According to Mixed Metal Ion The psicose conversion ratio in the composition similar to the fructose raffinate obtained in the psicose preparation process was evaluated. That is, the psicose conversion process was confirmed by diluting the syrup of fructose purity 95% by weight syrup to 50% by weight and adding $Ca^{2+}$ ion by 0.005~0.01 mM, and then additionally adding 1.0 mM of Mn, and shown in Table 7.

TABLE 7

| Ca ion concentration | Mn ion concentration | Relative activity compared to non-additive control group (%) |
|---|---|---|
| non-additive | non-additive | 100.00 |
| non-additive | 1.0 mM | 152.0 |
| 0.005 mM | 1.0 mM | 141.2 |
| 0.008 mM | 1.0 mM | 136.5 |
| 0.010 mM | 1.0 mM | 127.1 |

It was demonstrated that the relative activity of 152% under the treatment of manganese increasing the activity of psicose conversion reaction, was reduced by about 16% at the maximum when the addition of calcium. The relative activity tended to be reduced gradually as the concentration of calcium ion was increased.

This result shows why it is necessary to purify Ca ion of 0.01 mM or lower precipitated in the separation chromatography process, in reusing the fructose raffinate obtained in the high purity separation chromatography process. In case of no ion purification of fructose raffinate, the activity is lower than the case of using only manganese, thereby negatively affecting the yield of psicose.

The invention claimed is:

1. A method of preparation for psicose comprising: separating psicose conversion product of a psicose conversion reaction with a simulated moving bed (SMB) chromatography separation process to obtain a psicose fraction and a fructose raffinate, and recycling the fructose raffinate as a first fructose raw material into the psicose conversion reaction, mixing the fructose raffinate with a fresh fructose raw material as a second fructose raw material, before being recycled to the psicose conversion reaction, wherein a mixing ratio of the fructose raffinate and the second fructose raw material (raffinate:second fructose raw material) is a volume ratio of 1:0.9 to 1.5, when the fructose raffinate and the second fructose raw material have 50 Brix.

2. The method of preparation of claim 1, wherein the psicose conversion product is obtained by a biological psicose conversion process using fructose-containing raw material.

3. The method of preparation of claim 1, wherein a mixing ratio of the fructose raffinate and the second fructose raw material (raffinate:second fructose raw material) is a volume ratio of 1:0.95 to 1.15 or 1:1.05 to 1.2, when the fructose raffinate and the second fructose raw material have 50 Brix.

4. The method of preparation of claim 1, wherein the fructose raffinate is treated by performing one or more step selected from the group consisting of cooling, pH adjustment, ion purification and concentration, before being recycled to the psicose conversion reaction.

5. The method of preparation of claim 4, wherein the product treated by the ion purification has an electric conductivity of 0 to 15 μs/cm (microsiemens per centimeter).

6. The method of preparation of claim 1, wherein the fructose raffinate obtained in the SMB chromatography separation process has an electric conductivity of 20 to 200 μs/cm (microsiemes per centimeter).

7. The method of preparation of claim 1, wherein the method further comprises a step of ion purification step for adjusting the fructose raffinate in the mixture such that the mixture has an calcium ion concentration of 0.05 mM (millimolar) or lower, before being recycled to the psicose conversion reaction.

8. The method of preparation of claim 4, wherein the cooling is performed by a step of cooling the fructose raffinate obtained in the SMB chromatography separation process with a heat exchanger.

9. The method of preparation of claim 1, wherein the fructose content of fructose-containing raw material supplied to the psicose conversion reaction is 85 wt % or higher based on the 100 wt % of the total saccharides content in the fructose raffinate.

10. The method of preparation of claim 1, wherein the fructose raffinate obtained in the SMB chromatography separation process contains 85 to 98 wt % of fructose content and 2.0 wt % or lower of psicose content, based on the 100 wt % of the total saccharides content in the fructose raffinate.

11. The method of preparation of claim 1, wherein the method further comprises a step of adjusting a temperature, or controlling an input amount of fructose raffinate supplied to the psicose conversion reaction, after supplying the fructose raffinate into a storage tank.

12. The method of preparation of claim 1, wherein the method further comprises a step of ion purification of the fructose raffinate (1) before, or after the SMB chromatography separation process, or (2) both before and after the SMB chromatography separation process.

13. The method of preparation of claim 1, wherein the SMB chromatography separation process is carried out by a chromatographic column packed with a cation exchange resin having an attached calcium active group.

14. The method of preparation of claim 1, wherein the psicose conversion reaction is performed by using a biological catalyst having a psicose conversion rate of 15% to 70%.

15. The method of preparation of claim 1, wherein the method is performed continuously.

16. The method of preparation of claim 1, wherein the method further comprises a step of concentrating the psicose fraction and crystallizing the psicose from the concentrated psicose fraction to obtain psicose crystal and crystallization mother liquor.

* * * * *